United States Patent [19]

Osawa

[11] Patent Number: 4,978,658
[45] Date of Patent: Dec. 18, 1990

[54] COMPOSITIONS CONTAINING 5α-DIHYDRO-19-NORETHISTERONE AND DERIVATIVES THEREOF FOR IN VIVO INHIBITION OF AROMATASE

[75] Inventor: Yoshio Osawa, Buffalo, N.Y.

[73] Assignee: Medical Foundation of Buffalo, Inc., Buffalo, N.Y.

[21] Appl. No.: 257,723

[22] Filed: Oct. 14, 1988

Related U.S. Application Data

[63] Continuation of Ser. No. 19,338, Feb. 26, 1987, Pat. No. 4,829,059.

[51] Int. Cl.$^5$ .......................... A61K 31/56; C07J 1/00
[52] U.S. Cl. ...................................... 514/178; 552/649
[58] Field of Search ...................... 514/178; 260/397.4

[56] References Cited

PUBLICATIONS

Yoshio Osawa et al.; Irreversible Inhibitors of Oestrogen...; Biochemical Society Transactions, vol. 11, pp. 656–659 (1983).

Primary Examiner—Joseph A. Lipovsky
Attorney, Agent, or Firm—Oblon, Spivak, McClelland, Maier & Neustadt

[57] ABSTRACT

A composition for in vivo inhibition of aromatase in a mammal, which comprises an in vivo inhibitory amount of a compound having the following general formula:

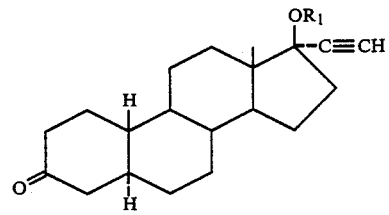

wherein $R_1$ is hydrogen or $C_{1-4}$ acyl, in combination with as pharmaceutically acceptable carrier or diluent thereof.

14 Claims, 14 Drawing Sheets

COMPOSITIONS CONTAINING 5α-DIHYDRO-19-NORETHISTERONE AND DERIVATIVES THEREOF FOR IN VIVO INHIBITION OF AROMATASE

The investigations leading to this invention were supported in part by NIH research grant No. HD04945.

This is a continuation of application Ser. No. 07/019,338, filed Feb. 26, 1987, now U.S. Pat. No. 4,829,059.

BACKGROUND OF THE INVENTION

1. Field of the Invention

This invention relates to compositions containing 5α-dihydro-19-norethisterone (5α-DHNET) and its acyl derivatives as in vivo inhibitors of the enzyme aromatase. As a result of this enzyme inhibitory effect, the present compositions can be used to prevent and treat endocrine dependent conditions such as gynocomastia, and estrogen-dependent breast or uterine cancers.

2. Discussion of the Background

Aromatase is an enzyme which catalyzes the conversion of androgen into estrogen, the terminal aromatization step of estrogen biosynthesis. It is a membrane-bound complex system, which catalyzes a series of reaction steps with multiple mono-oxygenations. Because of the complexity of the system, the precise pathway or reaction mechanism of aromatization has not yet been established, nor has the isolation of pure enzyme been achieved. At least two distinct forms of human placental aromatase are known. See Osawa and Higashiyama, in Microsomes, Drug Oxidations, and Chemical Carcinogenesis (Coon, M. J. et al.), volume 1, pp. 225–228, Academic Press, London and New York (1980).

The product of aromatase action, estrogen, is not only essential for reproduction and development but also promotes the growth of estrogen dependent cancers.

Approximately one third of the cases of human breast cancers require the female hormone estrogen for their growth and regress when the tumors are deprived of the hormone. Removal of the source of estrogen is an effective method of treating breast cancers, and other endocrine-dependent cancers including uterine cancer.

The ovary is the major source of estrogen in premenopausal women and oophorectomy (excision of the ovary) is the classical treatment of premenopausal patients with advanced breast cancer. In postmenopausal patients, the sites of estrogen biosynthesis are peripheral tissues such as fat, skin, muscle, and the tumor itself, where the conversion of androgen to estrogen is catalyzed by aromatase. These peripheral tissues are not subject to excision by surgical methods, but their aromatase activity may be chemically inhibited by use of aromatase inhibitors. Several agents, such as aminoglutethimide, testololactone, and 4-hydroxyandrostenedione, which have been used to successfully treat breast cancer, are aromatase inhibitors. However, these drugs are not particularly specific or highly potent, and they have deleterious side effects. There is, therefore, a need to develop better agents with fewer side effects for long term treatment to prevent the onset and growth of endocrine-dependent tumors. In this respect, 5α-DHNET was found to be particularly valuable by in vivo pharmacological studies.

Another condition associated with an imbalance in the amount of estrogen is known as gynecomastia. This is a pathological condition resulting in enlargement of the male breast. In gynecomastia, due either to normal or abnormal causes the enlargement is believed to result from disturbance of the normal ratio of active androgen to estrogen in plasma or within the breast itself. In men given diethylstilbestrol, histological changes in the male breast resemble those in other forms of clinical gynecomastia, a finding in keeping with the concept that gynecomastia is the result of an estrogen effect. Estradiol formation in the normal man occurs principally by the conversion of circulating androgens to estrogens in peripheral tissues. Feminization results when there is a significant decrease in the ratio of production of testosterone to estradiol, and this may be a result of diminished testosterone production or action, enhanced estrogen formation, or both processes occurring simultaneously. Inhibitors of aromatase would have an inhibitory effect on gynecomastia when the condition is associated with enhanced estrogen formation in the male.

5α-DHNET is a reduction product of the contraceptive progestogen, norethisterone. The structure of this compound is as follows:

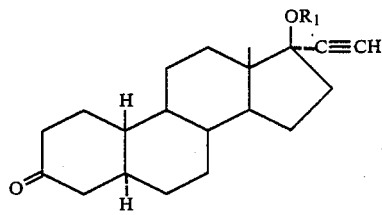

wherein R, is hydrogen.

It is a known compound which has been synthesized as an intermediate from norethisterone by reduction with lithium in liquid ammonia (A. Bowers, H. J. Ringold and E. Denot, J. Am. Chem. Soc. 80, 6115–6118 (1958)). Bowers et al reported no utility whatsoever for this compound. Unlike norethisterone, 5α-DHNET is not aromatizable by aromatase due to the saturation of the 4-double bond and thus it does not possess the adverse consequence of being converted to an estrogenic substance after being given to the patient. This compound is the major reduced metabolite in humans of norethisterone which has been widely administered on a long term basis to women of reproductive age for the past thirty years as the major ingredient of the contraceptive pill. Thus, it has been shown that the compound is safe for treatment of human subjects even in the long term.

A number of substrate analogs have been evaluated as competitive inhibitors of aromatase in vitro (see Schwarzel et al., Endocrinology (Baltimore) 92, 866–880 (1973)). 4-Hydroxyandrostenedione has been found to cause regression of estrogen-dependent breast cancers of rats (Brody et al., Endrocrinology (Baltimore) 100, 1684–1695 (1977)).

Generally, irreversible inhibitors are expected to be more effective for use in vivo if they are targeted selectively toward the enzyme. Mechanism-based or suicide inactivators are designed to achieve a high degree of selectivity of irreversible inhibition through a covalent-bond formation at the active site of the enzyme, but before such compounds are acted upon by the target enzyme they are relatively unreactive and are therefore not likely to form covalent bonds with other cellular components indiscriminantly. In fact, they carry a latent reactive functional group which is transformed through normal catalytic activity of the target enzyme into the reactive species. This activation occurs after a formation of the enzyme-inhibitor complex and therefore the activated inhibitor has a better chance to make a covalent bond connection to a reactive group of the enzyme at or near the active site resulting in selective inactivation of the enzyme. The compound norethisterone (17α-ethynyl-19-nortestosterone) is a suicide inactivator of aromatase. 5α-DHNET has now been discovered to be an in vivo inhibitor of aromatase and it is suspected that such inhibition occurs through a mechanism based reaction.

5α-DHNET was previously found to be a very weak in vitro aromatase inhibitor (Y. Osawa, Y. Osawa, C. Yarborough & L. Borzynski, Biochem Soc. Transactions, 656–659 (1983)), requiring a 50 μM concentration for a partial inhibition of human placental aromatase in vitro. This compares to 0.0082 μM and 0.056 μM for 6α- and 6β-bromoandrostenedione by the in vitro assay with human placental aromatase (S. J. Santner, H. Rosen, Y. Osawa & R. J. Santen, J. Steroid Biochem. 20, 1239–1242 (1984)) and indicates that 5α-DHNET is a thousand-fold less potent aromatase inhibitor in in vitro assays.

The potent in vivo aromatase inhibitory activity of 5α-DHNET and suppression of the growth and incidence of breast carcinomas in experimental animals as shown in the following Examples were totally unexpected and could not be deduced by inference from the previous in vitro studies. Indeed, the in vitro studies showed 5α-DHNET to be essentially inactive; certainly not a candidate for in vivo activity. Thus, the properties of 5α-DHNET, which make it useful as an inhibitor of aromatase in vivo and as a drug for treatment and suppression of the incidence of certain endocrine-dependent cancers, were found for the first time by this invention. In general, although a variety of compounds have been shown to be in vitro aromatase inhibitors and have therefore been considered potential candidates for in vivo activity, it can now be seen that in vitro activity provides no assurance of in vivo activity.

SUMMARY OF THE INVENTION

It is an object of the present invention to provide compositions for the in vivo inhibition of aromatase.

Another object of this invention is to provide a method for in vivo inhibition of aromatase.

It is yet another object of the present invention to provide a method of treatment or prevention of endocrine-related conditions.

It is yet another object of this invention to provide compositions for treatment or prevention of endocrine-related conditions.

These and other objects as will hereinafter become more readily apparent, have been achieved by providing compositions containing 5α-DHNET and acylated derivatives thereof. Such compounds, as discussed above, have been found to possess in vivo activity as inhibitors of aromatase. Moreover, such compositions have been demonstrated to exert in vivo activity in appropriate animal models against endocrine-related cancers. In particular, breast cancer and uterine cancer are candidates for treatment with such compositions. Other endocrine dependent conditions such as gynocomastia, precocious puberty, endometriosis, and feminizing adrenal tumors are similarly treatable or preventable with the compositions of this invention. Also provided herein is a method of treating such conditions which involves treatment of a mammal such as a human with an appropriate dosage amount of 5α-DHNET or a derivative thereof.

BRIEF DESCRIPTION OF THE DRAWINGS

A more complete appreciation of the invention and many of the attendant advantages thereof will be readily obtained as the invention becomes better understood by reference to a detailed description when considered in connection with the accompanying drawings, wherein.

DESCRIPTION OF THE PREFERRED EMBODIMENTS

Figure 1:
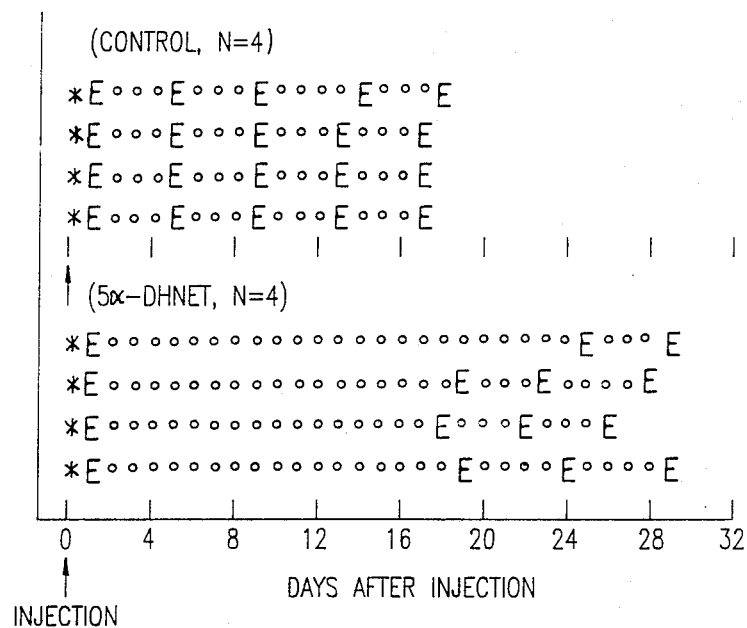
FIG. 1 shows the effect of 5α-DHNET on the rat estrus cycle.

The present invention is based on the discovery that 5α-DHNET and its acylated derivatives are capable of inhibiting in vivo the enzyme aromatase.

The structure of 5α-DHNET and its related derivatives is as follows:

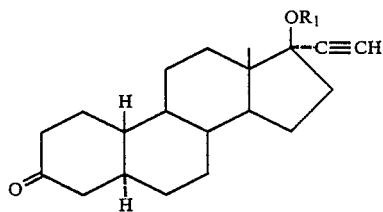

wherein $R_1$=H or $C_{1-4}$. Acyl derivatives of 5α-DHNET may be, for example, acetate, propionate, butyrate, etc. The acyl derivatives may act as prodrugs; that is, the acyl moiety may be cleaved off of the molecule in vivo by the action of enzymes or otherwise, to result in active 5α-DHNET. Thus, these acyl derivatives acting as prodrugs would give rise to sustained activity. In addition, the acyl derivatives may themselves be active against endocrine-dependent conditions and may inhibit aromatase in vivo.

The preparation of the compounds according to the present invention may be based on the method described in Ringold, J. Am. Chem. Soc. 80, 6115–6118 (1958). Each of the reactions involved in the synthetic scheme may be readily optimized by one of ordinary skill in the art based on basic synthetic organic chemistry. The choice of solvents, temperatures, and other reaction conditions may be readily ascertained without undue experimentation. Acylated derivatives of 5α-DHNET may be prepared by methods of acylation which are well known to one of ordinary skill in the area of synthetic organic chemistry.

The compounds of the present invention are notably non-toxic in vivo. For example, the minimum lethal dose of 5α-DHNET for SD rat (SPF) is greater than 5,000 mg/kg. Accordingly, host toxicity does not appear to be a problem with the compounds and compositions described herein.

As used herein, aromatase, or estrogen synthetase, is the enzyme complex which catalyzes the final step in the biosynthetic sequence from cholesterol to the estrogens. See Bellino and Osawa, Biochemistry, 13, 1925–1931 (1974). At least two forms of the enzyme complex have been isolated from human placenta. See T. Higashiyama and Y. Osawa, Fed. Proc. Fed. Am. Soc. Exp. Biol. 42, 1836 (Abst. 458) (1983); Y. Osawa and T. Higashiyama in Microscomes, Drug Oxidations and Chemical Carcinogenesis (M. J. Coon etal., eds.) Vol. 1, 225–228, Academic Press, London and New York (1980); Y. Osawa et al., J. Steroid Biochem. 15, 4490452 (1981); Y. Osawa et al. in Microsomes, Drug Oxidations and Drug Toxicity (R. Sato and R. Kato, eds.) 315–316, Japan Scientific Society Press, Tokyo (1982); and Y. Osawa et al., Cancer Res. 42 (Suppl), 3299s–3396s (1982).

Methods for measuring the ability of 5α-DHNET and its related acylated derivatives to inhibit aromatase in vivo are described in the examples hereinbelow.

Mammals such as humans suffering from endocrine-related conditions, particularly estrogen-dependent breast cancers and uterine cancers, and gynocomastia, can be treated by adminstering to the patient a pharmaceutically effective amount of one or more of the present compounds in the presence of a pharmaceutically acceptable carrier of diluent. Mammals suspected of being at an elevated risk of becoming afflicted by an endocrine-dependent condition, such as being a member of a family in which other members have been afflicted by an endocrine-dependent condition, may also be treated by administering a preventive amount of a composition according to this invention.

Macklin clearly indicated in 1959 that breast cancer patients had a higher incidence of breast cancer among their maternal and paternal grandmothers and aunts as well as among their mothers and sisters (Macklin, M. T., Comparison of the Number of Breast Cancer Deaths Observed in Relatives of Breast Cancer Patients, and the Number Expected on the Basis of Mortality Rates, J. Natl. Cancer Inst. 22, 927–951 (1959)).

According to the American Cancer Society's estimate, there will be 130,000 new breast cancer patients in 1987 in the United States alone, and the chance of becoming afflicted with breast cancer for American women in their lifetime is approaching one in every ten women. Deaths due to breast cancer are estimated to be 41,300 during 1987 in the United States.

Black et al in recent studies involving more than one thousand patients with invasive breast cancers during 1970–1984 (M. M. Black and R. E. Zachrau, Family History and Hormones in Stepwise Mammary Carcinogenesis, Annals New York Academy of Sciences, 464, 367–377 (1986)), reported that among unselected breast cancer patients, 20–39 years of age, 47% had a positive family history (FH) of breast cancer. More specifically, 36% of the patients had a grandmother and/or aunt (G/A) with breast cancer. The proportion of G/A-positive patients decreased progressively in each successive decade, down to a value of 4% among patients 60 years of age or older. Another feature, distinctive for young G/A-positive women, is the association with oral contraceptive usage. Sixty five percent of G/A-positive breast cancer patients were oral contraceptive-positive in contrast to 41% of G/A-negative patients ($p < 0.01$). The oral contraceptives contain orally potent estrogens. It appears that FH-associated differences exist in regard to hormone effects on the mammary parenchyma of young women. The data suggest that there are subpopulations of women whose mammary parenchyma is particularly susceptible to malignant transformation when they are young. Such susceptibility is preferentially found among women whose grandmothers or aunts had breast cancer. Such familial association appears to involve an unusual sensitivity to female sex hormones in the form of oral contraceptives. It further appears that such sensitivity is genetically rather than socially determined, since the involved relatives are equally likely to be paternal as well as maternal. Thus, it is suggested that women of reproductively active age who have FH of breast cancer among their maternal and paternal grandmothers and aunts as well as among their mothers and sisters may be a preferable select group of subjects for the 5α-DHNET treatment to lower incidence of breast cancers.

A retrospective case-control study was carried out also by Black et al to determine to what degree atypical changes in the mammary duct system are associated with increased risk of developing breast cancer (Black, Barclay, Cutler, Hankey, and Asire, Association of Atypical Characteristics of Benign Breast Lesions with Subsequent Risk of Breast Cancer, Cancer, 29, 338–343 (1972)). Their primary finding was that a woman with some degree of ductular atypia in a benign lesion is subject to a risk of developing breast cancer 5 times that of a woman with no evidence of atypical changes. Mammary carcinogenesis appears to be a stepwise phenomenon which involves recognizable precursor lesions, i.e., precancerous mastopathy and in situ carcinoma. Thus, women found to have some degree of ductular atypia in a benign lesion may also be selected as a preferable group for the 5α-DHNET treatment to prevent the precursor lesions from transforming to invasive breast cancer.

In animal studies, while oophorectomized rats showed a heavier body weight compared to that of the untreated controls over a several month period, the 5α-DHNET treated rats did not show any significant difference of body weight from the control rats.

A single injection of 5α-DHNET (50 mg/kg body weight) to normal 4-day cycling rats caused a cessation of the estrus cycle for 4 to 6 cycles (16 to 24 days), whereas the sesame oil-only controls and a group treated with the same dose of 6β-bromoandrostenedione, a potent in vitro aromatase inhibitor (R. M. Budnick & T. L. Dao, Steroids, 35, 533-541 (1980); S. J. Santner, H. Rosen, Y. Osawa and R. J. Santen, J. Steroid Biochem. 20, 1239-1242 (1984); Y. Osawa, M. J. Coon and Y. Osawa, Fed. Proc., 45, 1749, A-1564 (1986)) showed no effect on the cycle, as shown in Example 1. The four-day treatment of 4-day cycling rats with 5α-DHNET showed, as exhibited in Example 2, a significant 67% suppression (p<0.0005) of the ovarian aromatase activity. The in vivo action of 5α-DHNET was compared to those of 6α-bromoandrostenedione (only insignificant 10% suppression) and 6β-bromoandrostenedione (72% suppression), both of which are potent in vitro aromatase inhibitors as shown in the references cited above.

The compounds according to the present invention are generally included in a pharmaceutically acceptable carrier or diluent in an amount sufficient to exert a therapeutically useful in vivo inhibitory effect on aromatase.

There may also be included as part of the compositions pharmaceutically compatible binding agents, and/or adjuvant materials. The active materials can also be mixed with other active materials which do not impair the desired action and/or supplement the desired action. The active materials according to the present invention can be administered by any route, for example, orally, parenterally, intravenously, intradermally, subcutaneously, or topically, in liquid or solid form.

A preferred mode of administration of the compounds of this invention is oral. Oral compositions will generally include an inert diluent or an edible carrier. They may be enclosed in gelatin capsules or compressed into tablets. For the purpose of oral therapeutic administration, the aforesaid compounds may be incorporated with excipients and used in the form of tablets, troches, capsules, elixirs, suspensions, syrups, wafers, chewing gums and the like. The amount of active compound may be varied depending upon the particular form.

The tablets, pills, capsules, troches and the like may contain the following ingredients: a binder such as microcrystalline cellulose, gum tragacanth or gelatin; an excipient such as starch or lactose, a disintegrating agent such as alginic acid, Primogel, corn starch and the like; a lubricant such as magnesium stearate or Sterotes; a glidant such as colloidal silicon dioxide; and a sweetening agent such as sucrose or saccharin or a flavoring agent such as peppermint, methyl salicylate, or orange flavoring may be added. When the dosage unit form is a capsule, it may contain, in addition to material of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active compounds, sucrose as a sweetening agent and certain preservatives, dyes, colorings and flavors. Materials used in preparing these various compositions should be pharmaceutically pure and non-toxic in the amounts used.

For the purposes of parenteral therapeutic administration, the active ingredient may be incorporated into a solution or suspension.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic.

While dosage values will vary with the specific severity of the disease condition to be alleviated or the degree of risk of the patient of contracting an endocrine-dependent condition, good results are achieved when the compounds described herein are administered to a subject requiring such administration as an effective oral, parenteral or intravenous dose of from 1 to 500 mg/day per patient. A particularly preferred effective amount is about 5 to 250 mg/day per patient. A most preferred effective amount is about 10 to 150 mg/day per patient. These dosage ranges are what is meant by an in vivo aromatase inhibitory amount or an anti-(endocrine-dependent condition) amount of the present compositions. It is to be understood, however, that for any particular subject, specific dosage regimens should be adjusted to the individual need and the professional judgment of the person administering or supervising the administration of the aforesaid compound. It is to be further understood that the dosages set forth herein are exemplary only and they do not limit the scope or practice of the invention. The dosages may be administered at once, or may be divided into a number of smaller doses to be administered at varying intervals of time.

The invention now being generally described, the same will be better understood by reference to certain specific examples which are included herein for purposes of illustration only and are not intended to be limiting of the invention or any embodiment thereof, unless specified.

EXAMPLES

Overview of Examples

The effect of 5α-DHNET on the growth of endocrine-dependent breast cancers was assessed in BUF/N rats with breast carcinomas induced by N-nitrosomethylurea (NMU). 5α-DHNET at 50 mg/kg body weight/day was given daily for three weeks to rats already having at least one tumor, 2 cm or larger. The total volume and number of tumors were measured. The results showed, as provided in Example 3, that 5α-DHNET significantly suppressed the growth of breast carcinomas while untreated animals showed a rapid tumor growth. The preventive effect of 5α-DHNET on the incidence and development of breast cancers was assessed by giving carcinogen primed animals 5α-DHNET for a one week period at 50 mg/kg body weight/day before any breast tumor was detectable. Oophorectomy is known to lower the incidence and death rate due to breast carcinomas in this animal model (P. M. Gullino, H. M. Pettigrew, and F. H. Grantham, J. Natl. Cancer Institute, 54, 401-409 (1975)). As shown in Examples 4-6, 5α-DHNET given at different times was found in all cases to significantly lower the incidence of breast carcinoma and the death rate as effectively as complete oophorectomy.

An observation at the 98th day after the initial NMU injection under the first protocol of 5α-DHNET treatment for the prevention of breast carcinoma development, as described in Example 4, gave a tumor incidence of 13% (2/16) for the 5α-DHNET treated group compared to 100% (16/16) for the control group and 38% (6/16) for the oophorectomized group. The death rate observed at the 180th day after the first injection of NMU was 25% (4/16), 31% (5/16), and 69% (11/16) for the 5α-DHNET treated, oophorectomized, and control groups, respectively. These in vivo studies, therefore, indicate that 5α-DHNET may be effectively and safely used for the prevention and treatment of breast cancers.

Biological Evaluation of 5α-DHNET

EXAMPLE 1

Effect of 5α-DHNET on the Estrus Cycle

Figure 2:
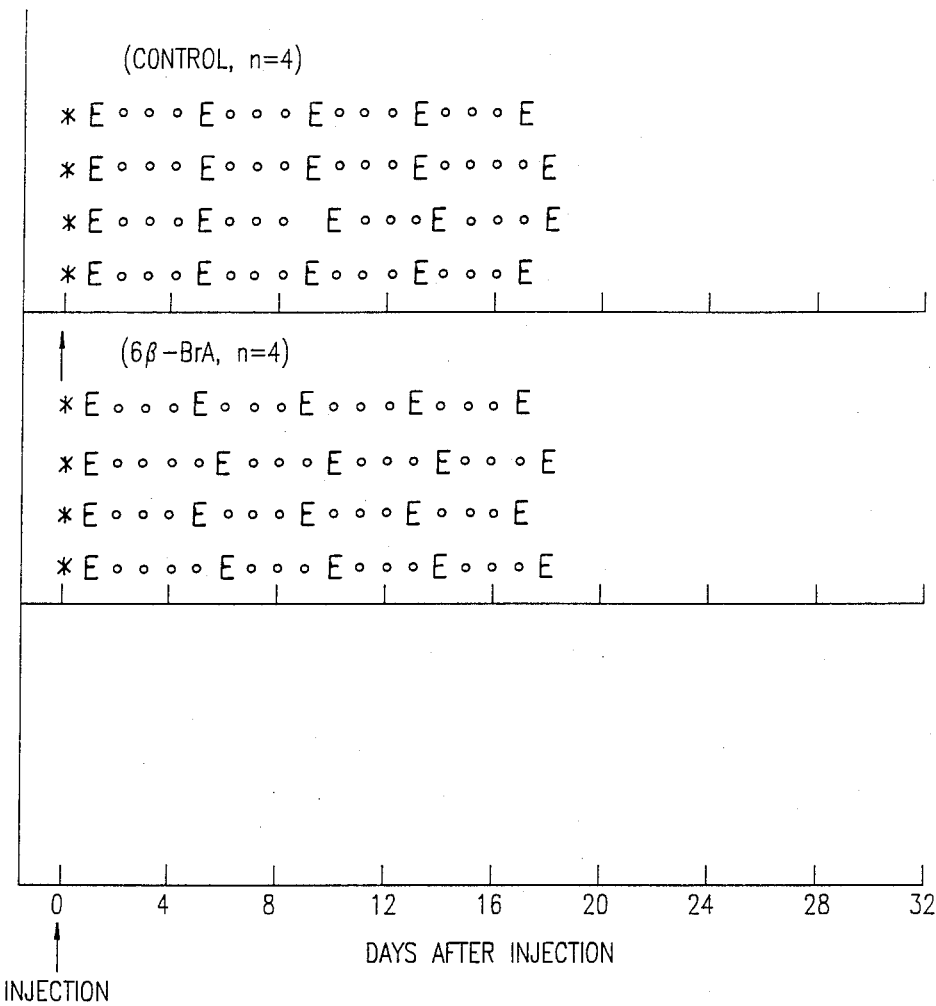
FIG. 2 shows the effect of 6β-bromoandrostenedione on the rat estrus cycle.

BUF/N inbred female rats (50–80 days old) showing regular 4-day estrus cycles were selected by a daily vaginal smear test. A fine powder of the steroid sample was suspended in sesame oil (30 mg/ml) and injected subcutaneously on the proestrus day at a single dose of 50 mg/kg body weight. Vaginal smears were examined daily until normal estrus returned for at least three cycles. The results from the single injection of 5α-DHNET are given in FIG. 1 and those for 6β-bromoandrostenedione are given in FIG. 2 for comparison. 5α-DHNET caused a cessation of the estrus cycles for at least four cycles on all of the animals tested (4/4). In contast, 6β-bromoandrostenedione, a known potent in vitro aromatase inhibitor, failed to affect the estrus cycle.

EXAMPLE 2

In Vivo Effect of 5α-DHNET on the Ovarian Aromatase Activity

Figure 3:
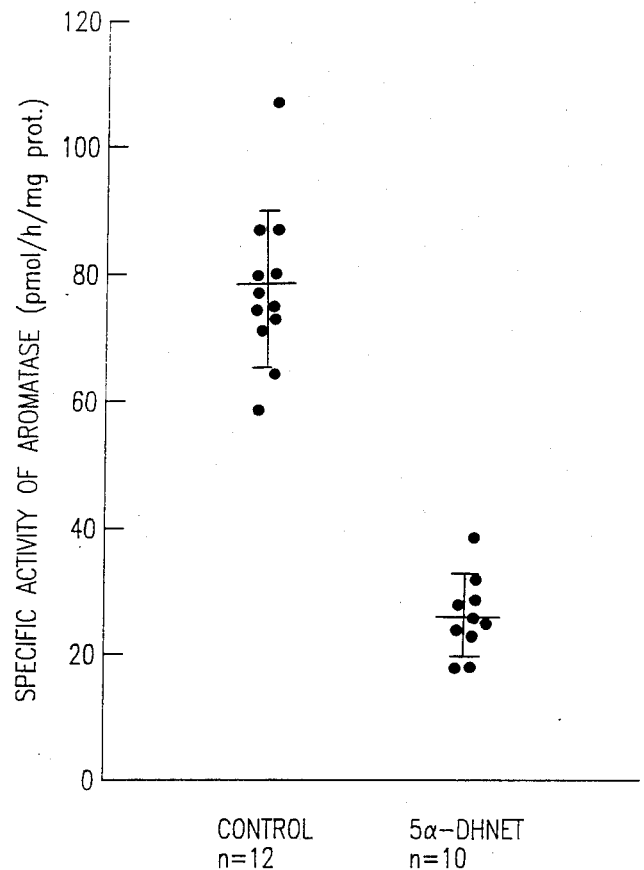
FIG. 3 show the in vivo effect of 5α-DHNET on rat ovarian aromatase activity.
Figure 4:
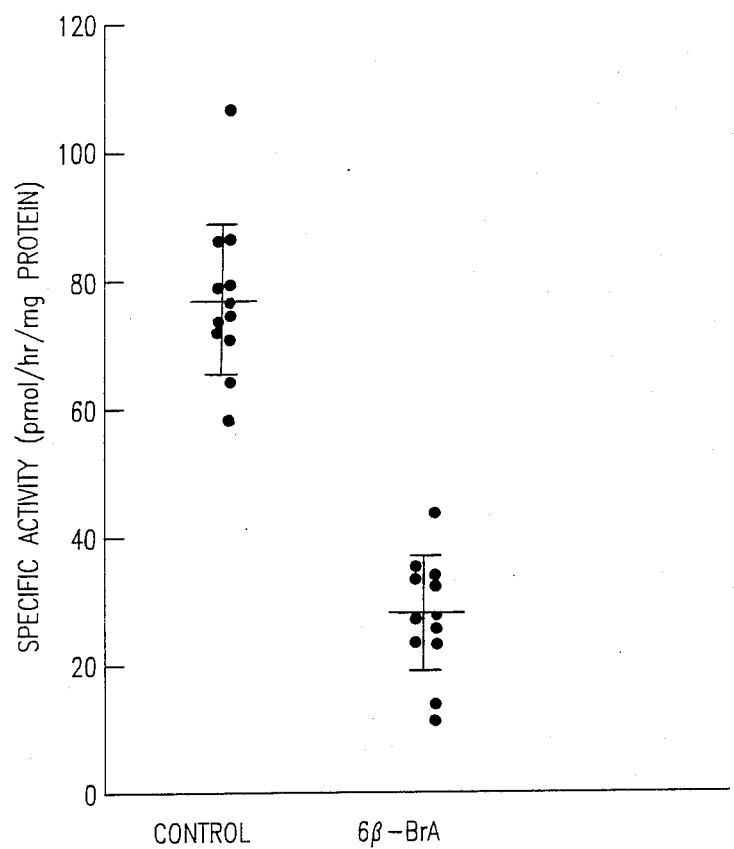
FIG. 4 shows the in vivo effect of 6β-bromoandrostenedione on rat ovarian aromatase activity.
Figure 5:
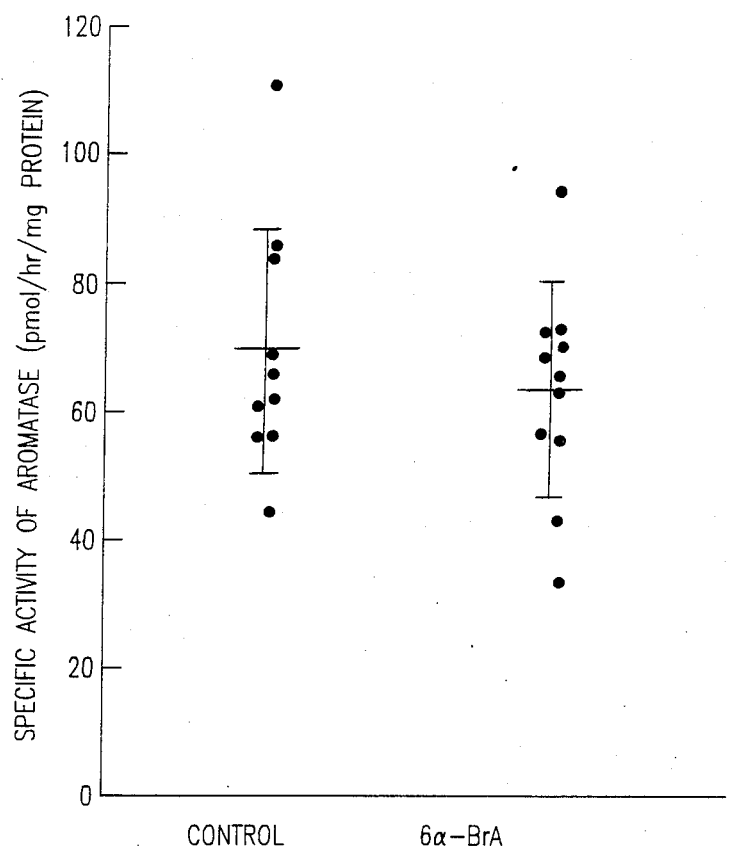
FIG. 5 shows the in vivo effect of 6α-bromoandrostenedione on rat ovarian aromatase activity.

5α-DHNET (30 mg/ml sesame oil suspension) was injected s.c. twice daily for four days at a dose of 50 mg/kg body weight/day to BUF/N inbred female rats (50–80 days old) showing regular 4-day estrus cycles starting on the estrus day. The control group received injections of sesame oil in the same manner. Both ovaries were removed 3–4 hours after the final injection. The 105,000 xg precipitate fraction of the ovarian homogenate was used for the aromatase assay. Aromatase activity was determined by the $^3$H-water method (F. L. Bellino, S. S. H. Gilani, S. S. Eng, Y. Osawa and W. L. Duax, Biochemistry, 15, 4730–4736 (1976)). The sedimented ovarian enzyme preparation was homogenized in 0.1M phosphate buffer (pH 7.5) and incubated with [1β-$^3$H, 4-$^{14}$C]androstenedione (3.18×10$^5$ dpm $^3$H, 1.18×10$^4$ dpm $^{14}$C, 100.2 ng), NADPH (1 mg) and BSA (5 mg) in 0.1M phosphate buffer (pH 7.5) in a total volume of 1.5 ml for 30 min at 37° C. Trichloroacetic acid solution (0.2 ml of 10% aqueous solution) was added to stop the enzyme reaction. Activated charcoal was added to the mixture and the spun supernatant was passed through a cotton plugged disposable pipet. The filtrate was counted for simultaneous $^3$H and $^{14}$C in a liquid scintillation spectrophotometer. The $^3$H-water released from the 1β-$^3$H labeled androgen quantitatively corresponds to estrogen formation. The results of the in vivo aromatase suppression assay with 5α-DHNET, 6β-bromoandrostenedione (6β-BRA), and 6α-bromoandrostenedione (6α-BRA) are given in FIGS. 3, 4, and 5, respectively. 5α-DHNET suppressed 67% of the ovarian aromatase, whereas 6β-bromoandrostenedione suppressed 72% and 6α-bromoandrostenedione only an insignificant 10%.

EXAMPLE 3

Effect of 5α-DHNET on Growth of Breast Carcinomas

Figures 6A, 6B:
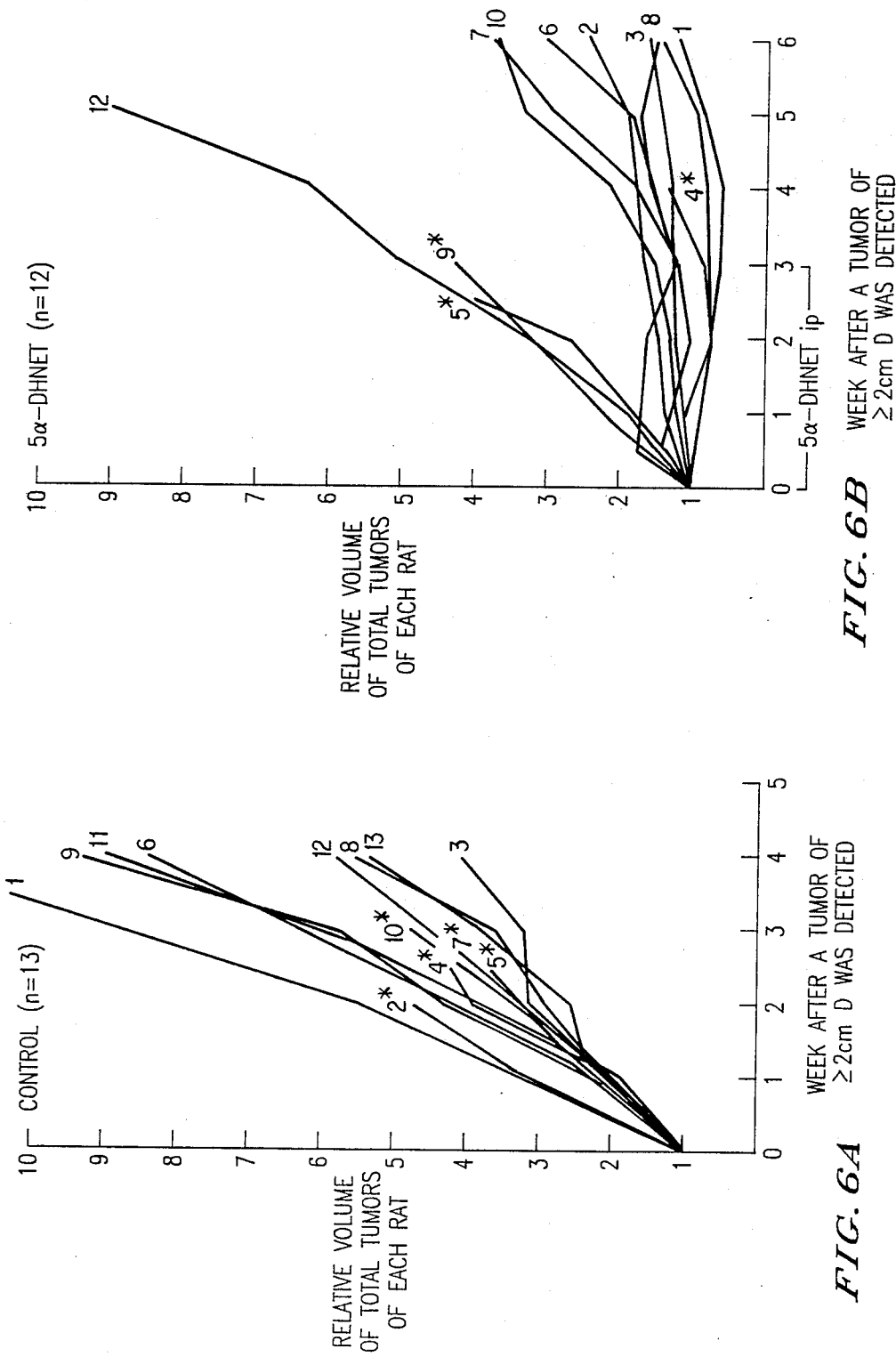
FIG. 6 shows the effect of 5α-DHNET on the growth of NMU-induced breast carcinomas of BUF/N rats in vivo.
Figure 7:
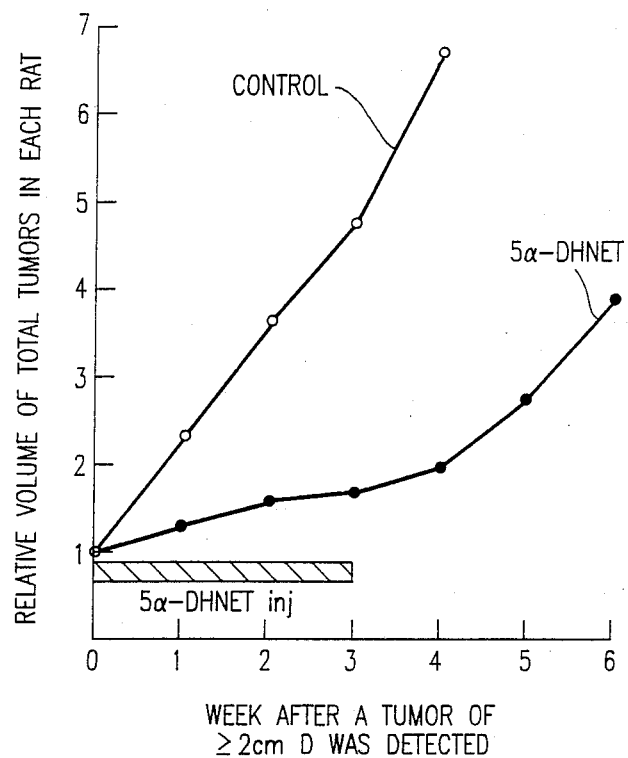
FIG. 7 shows the effect of 5α-DHNET in vivo on NMU-induced breast carcinomas of BUF/N rats.

The animal model for human mammary carcinomas developed by Gullino et al. (P. M. Gullino, H. M. Pettigrew, and F. H. Grantham, J. Natl. Cancer Inst., 54, 401–414 (1975)) was used for this evaluation of 5α-DHNET. N-Nitrosomethylurea (NMU), wet with 3% acetic acid, was dissolved in distilled water (10 mg/ml) and given in three intravenous injections at a dose of 50 mg/kg body weight to BUF/N inbred female rats of 50 days of age on the first injection. The second injection was 4 weeks and the third injection was 8 weeks after the initial administration. The onset of tumors was monitored by daily visual inspection and by palpation of the mammary regions three times a week. The increase in tumor size was monitored by vernier caliper measurements of the subcutaneous mass. One-half the average of the longest and shortest tumor diameters was taken as the value of r in the formula $4/3 \pi r^3$ used to estimate tumor volume. 5α-DHNET in sesame oil was given i.p. daily at a dose of 50 mg/kg body weight/day for 3 weeks to BUF/N female rats having at least one tumor, 2 cm or larger. The number and size of the tumors were monitored on 12 treated and 13 vehicle-only control animals. The mean initial volume of the tumors was 5.10 and 5.53 ml for the control and treated group, respectively. The results are given in FIGS. 6 and 7 and in Table 1. While the tumors in the control group grew very rapidly, growth arrest was clearly observed in 75% (9/12) of the treated group. The death rate was lower in the treated group (3/12 in 4 weeks) than in the control (5/13 in 3 weeks). After stopping the administration of 5α-DHNET, approximately half of the responded animals were maintained without a growth of tumors for another 3 weeks while the remainder showed a slow rate of tumor growth. Averaged relative tumor volume is compared in FIG. 7. This also indicates the suppression of tumor growth by the 5α-DHNET treatment. A summary of observations on each tumor at the end of treatment is given in Table 1. While 24 new tumors developed in 9 control rats in 3 weeks, only 7 developed in 11 treated rats. While 98% of tumors in the control rats grew and only 2% (1/53) regressed during the 3 week period, the treated group showed that 13% of the initially observed tumors had disappeared in the 3 week period and 42% of the tumors had regressed.

TABLE 1
EFFECT OF 5α-DHNET ON THE NUMBER OF NMU-INDUCED TUMORS IN BUF/N RATS

| | No. of Rats | Total No. of Tumors | | | | | |
|---|---|---|---|---|---|---|---|
| | | start | 3 wk | newly developed | growing | disappeared | regressed |
| Control | 9 | 29 | 53 | 24 | 52<br>52/53<br>(98%) | 0 | 1<br>1/53<br>(2%) |
| 5α-DHNET | 11 | 47 | 48 | 7 | 28<br>28/48<br>(58%) | 6<br>6/47<br>(13%) | 20<br>20/48<br>(42%) |

EXAMPLE 4
Effect of 5α-DHNET on the Incidence of Breast Carcinoma

Figure 8:
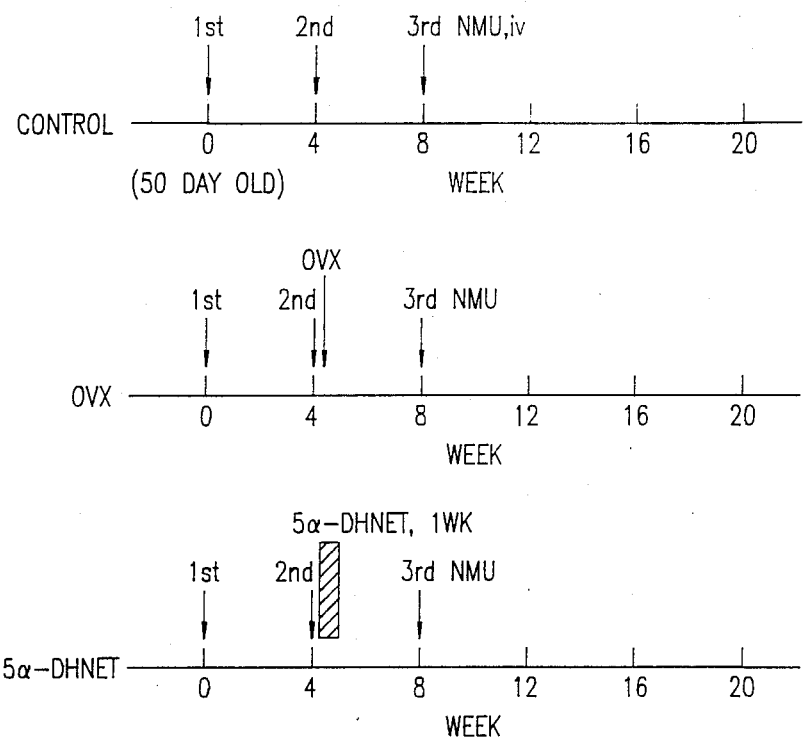
FIG. 8 shows the administration schedule of 5α-DHNET to NMU-induced BUF/N rats.
Figure 9:
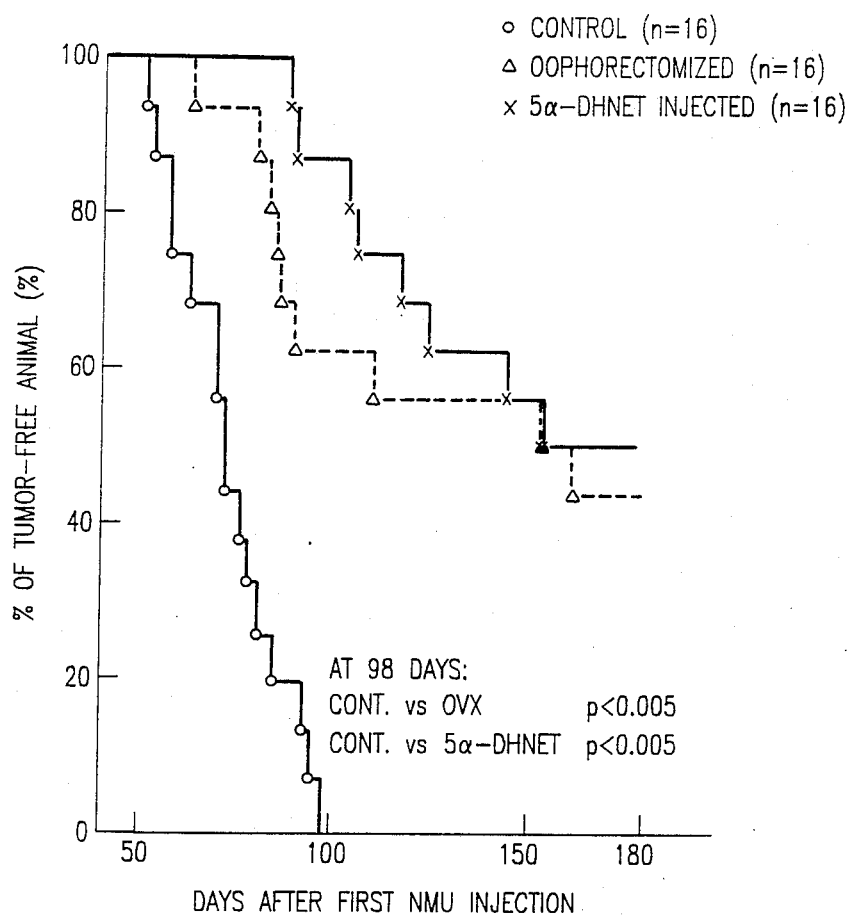
FIG. 9 shows the effect of 5α-DHNET and oophorectomy on breast tumor incidences of NMU-induced BUF/N rats.
Figure 10:
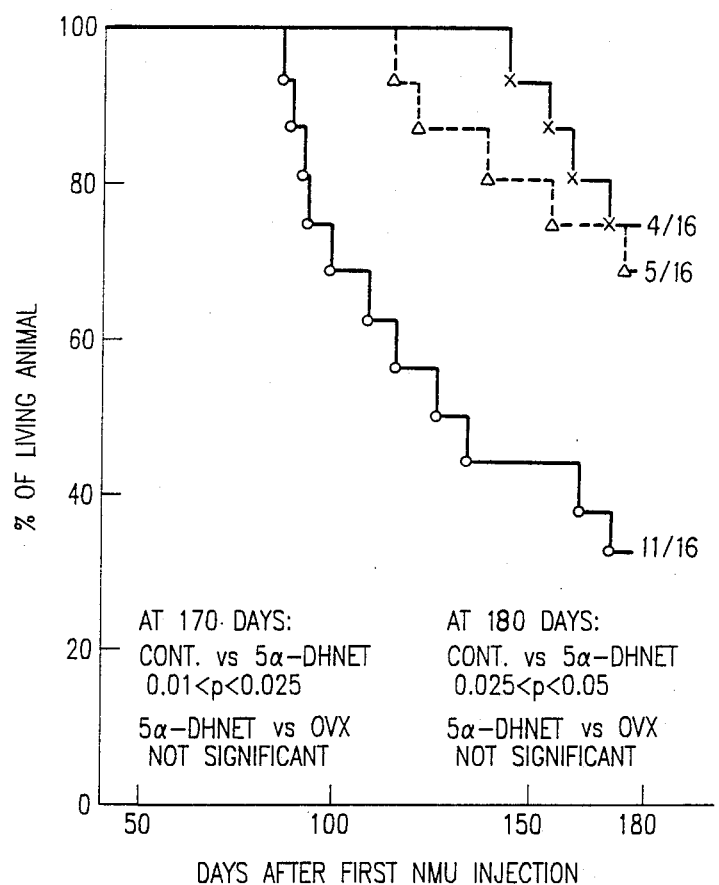
FIG. 10 shows the effect of 5α-DHNET and oophorectomy on the survival rate of BUF/N rats with NMU-induced breast carcinomas.

The preventive effect of 5α-DHNET to lower the incidence of breast carcinoma was assessed by use of the same animal model as in Example 3 but by modification of the administration protocol. The first protocol of 5α-DHNET administration and oophorectomy (OVX) is given in FIG. 8. The vehicle-only control was prepared as described in Example 3. Oophorectomy was carried out at the 4th week. 5α-DHNET at a dose of 50 mg/kg body weight/day was given i.p. daily for one week starting at the 4th week. The onset of tumors, their number and location in each animal were recorded daily. The results are given in FIGS. 9 and 10 and in Table 2. The control group developed tumors in 100% (16/16) of the animals by the 98th day after the first NMU injection. At this point tumor incidence for the 5α-DHNET treated and oophorectomized groups was 13% (2/16) and 38% (6/16), respectively. Both groups gradually increased the incidence and by the 180th day after the first NMU injection the 5α-DHNET and OVX group developed breast carcinomas in 50% (8/16) and 56% (9/16) respectively, as shown in FIG. 9. The death rate of the 5α-DHNET and oophorectomized groups were also significantly lower than that of the control. At the 180th day the death rate for the 5α-DHNET treated and oophorectomized group was 25% and 31%, respectively, compared to 69% for the control group. The mean latent period of tumor development was 72, 101, and 116 days for the control, OVX, and 5α-DHNET group, respectively. The average number of tumors per tumor carrying animal was 6.6, 2.0, and 1.8 for the control, OVX, and 5α-DHNET group, also showing that when 5α-DHNET was administered a long time prior to the detection of the tumor, it significantly supressed the development of the breast carcinomas.

TABLE 2
PREVENTIVE EFFECT of 5α-DHNET ON NMU-INDUCED TUMORS IN BUF/N RATS

| | % Tumor Incidence | Death | Mean Latent Period (days) | Average No. of tumors per tumor-carrying rat |
|---|---|---|---|---|
| Control | 16/16 (100%) | 11/16 (69%) | 72 | 6.6 |
| OVX | 9/16 (56%) | 5/16 (31%) | 101 | 2.0 |
| 5α-DHNET | 8/16 (50%) | 4/16 (25%) | 116 | 1.8 |

EXAMPLE 5
Effect of 5α-DHNET on the Incidence of Breast Carcinoma

Figure 11:
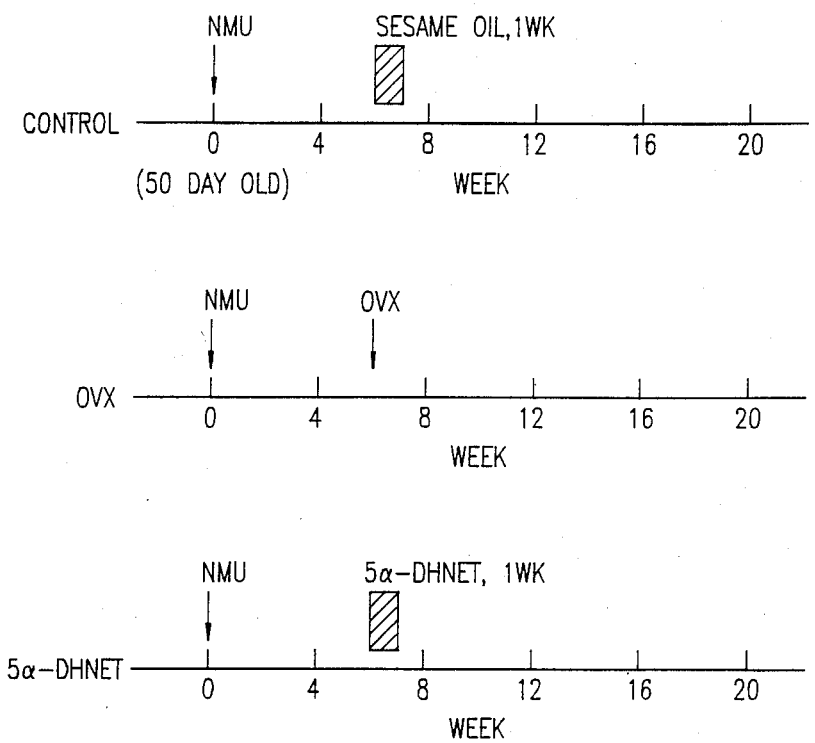
FIG. 11 shows the administration schedule of 5α-DHNET to NMU-induced BUF/N rats—protocol II.
Figure 12:
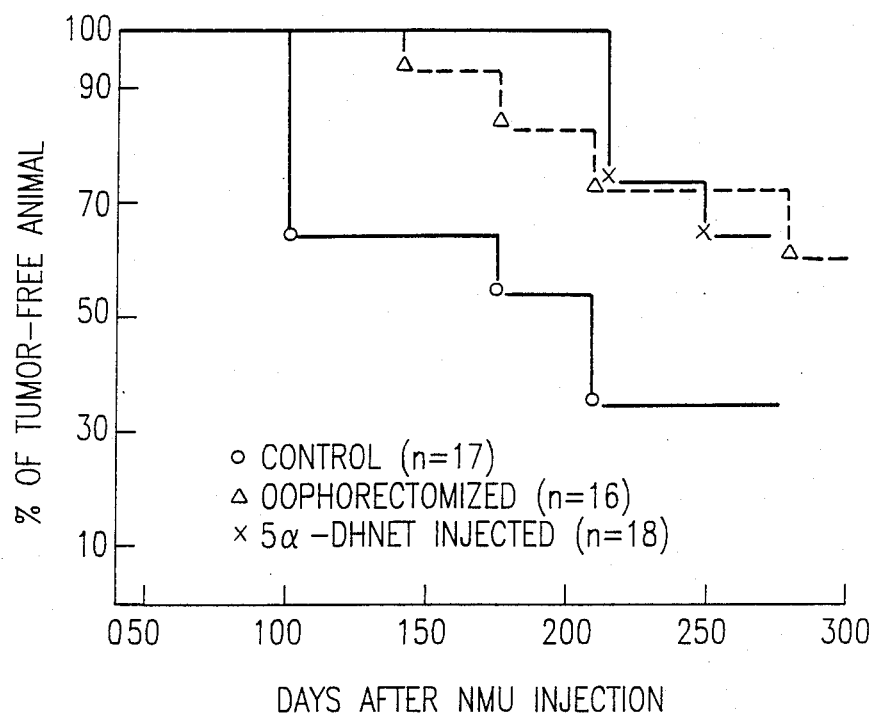
FIG. 12 shows the effect of 5α-DHNET on breast tumor incidence of NMU-induced BUF/N rats—protocol II.

The preventive and suppressive effect of 5α-DHNET on breast carcinomas was further examined in order to ascertain that this agent is effective under general conditions rather than limited to a specifically controlled protocol. Only a single dose of NMU was given to the BUF/N rats at 50th day of age and an oophorectomy was carried out at the 6th week after the NMU injection. The 5α-DHNET group received the agent for one week starting at the 6th week at a dose of 50 mg/kg body weight/day as given in FIG. 11. Monitoring was carried out as described in Example 4. The results are given in FIG. 12. After 41 weeks of observation, the tumor incidence was 65%, 33%, and 38% for the control, 5α-DHNET, and OVX group, respectively. The average number of tumors per tumor carrying rat was 2.6, 1.5, and 1.0 for the control, 5α-DHNET, and OVX group, respectively.

EXAMPLE 6
Effect of 5α-DHNET on the Incidence of Breast Carcinoma

Figure 13:
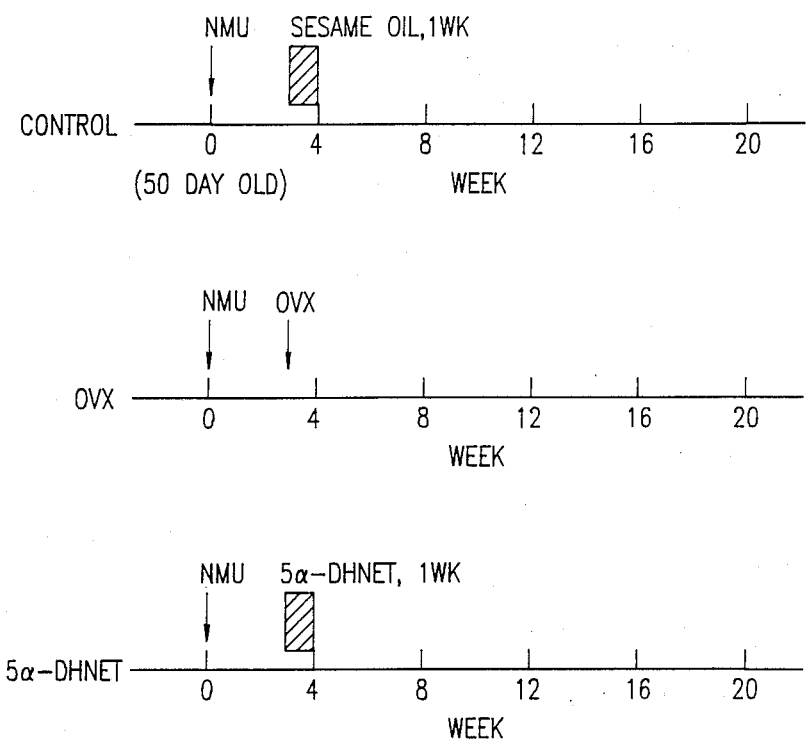
FIG. 13 shows the administration schedule of 5α-DHNET to NMU-induced BUF/N rats—protocol III.
Figure 14:
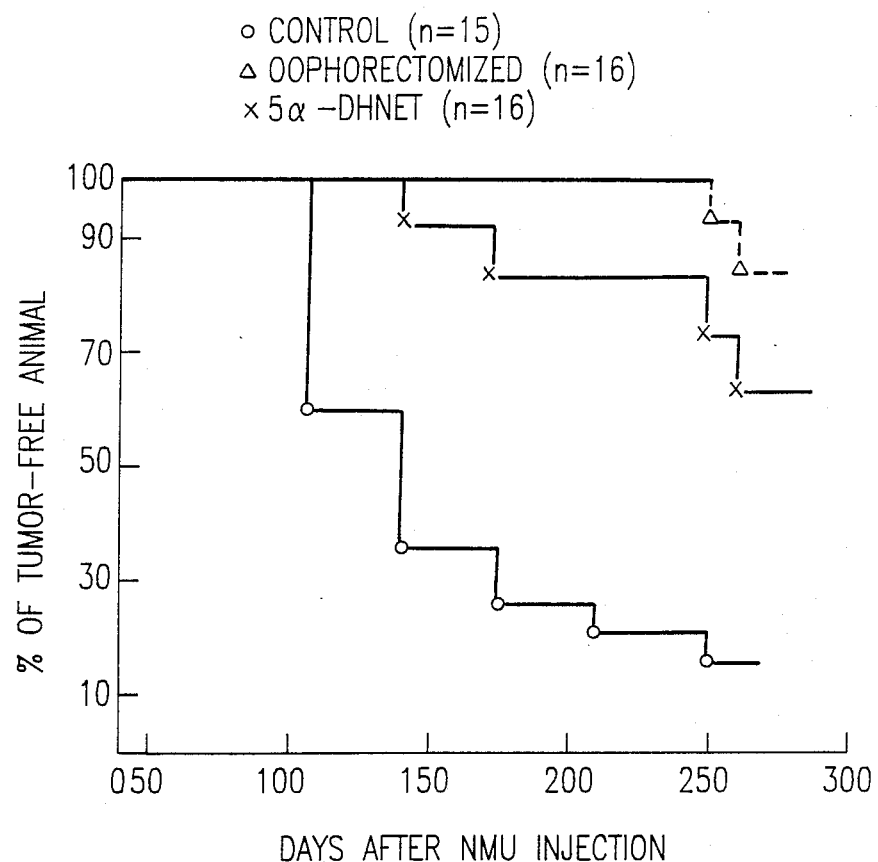
FIG. 14 shows the effect of 5α-DHNET on breast tumor incidence of NMU-induced BUF/N rats—protocol III.

The protocol was further modified to evaluate the generality of the effect of 5α-DHNET on breast carcinomas. As shown in FIG. 13, the 5α-DHNET treatment was given to rats 3 weeks after a single dose NMU injection. Oophorectomy was also carried out at 3 weeks after the NMU injection. The results are given in FIG. 14. After 37 weeks of monitoring, the tumor incidence was 87%, 38%, and 19% for the control, 5α-DHNET, and OVX group, respectively. The average number of tumors per tumor carrying animal was 2.8, 1.5 and 1.0 for the control, 5α-DHNET, and OVX group, respectively. The results indicate that 5α-DHNET given at any stage is effective in suppressing the development of breast condition and can be used in a general manner.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by letters patent of the United States is:

1. A composition for in vivo inhibition of aromatase in a mammal, which comprises an in vivo aromatase inhibitory amount of a compound having the following general formula:

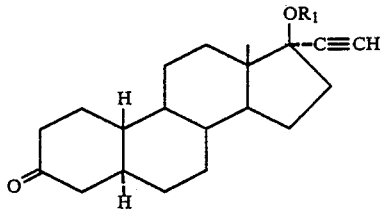

wherein $R_1$ is $C_{1-4}$ acyl, in combination with a pharmaceutically acceptable carrier or diluent thereof.

2. The composition of claim 1, wherein said composition is formulated for oral use.

3. The composition of claim 1, wherein said compound is included in said composition such that a unit dosage amount of said composition is 1 mg to 500 mg per day per patient.

4. A method of treatment or prevention of an endocrine-dependent condition in a mammal, which comprises administering to a mammal afflicted with an endocrine-dependent condition or in danger of becoming afflicted with an endocrine-dependent condition, an anti-(endocrine-dependent condition) effective amount of a composition containing a compound of the following general formula:

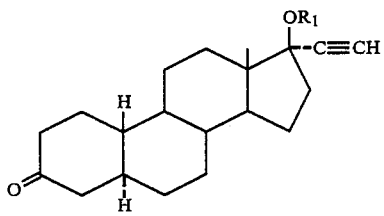

wherein $R_1$ is $C_{1-4}$ acyl, in combination with a pharmaceutically effective carrier or diluent.

5. The method of claim 4, wherein said mammal is a human.

6. The method of claim 4, wherein a unit dosage form of said composition delivers from 1 to 500 mg per day per patient of said compound.

7. The method of claim 4, wherein said composition is formulated for oral administration.

8. The method of claim 4, wherein said endocrine-dependent condition is breast cancer.

9. The method of claim 4, wherein said endocrine-dependent condition is uterine cancer.

10. The method of claim 4, wherein said endocrine-dependent condition is selected from the group consisting of gynocomastia, precocious puberty, endometriosis and feminizing adrenal tumor.

11. A method of inhibiting aromatase in vivo, which comprises administering to a mammal in need of said inhibition, a composition containing an active ingredient having the following general formula:

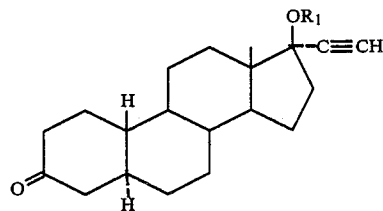

wherein $R_1$ is $C_{1-4}$ acyl, in combination with a pharmaceutically acceptable carrier or diluent.

12. The method of claim 11, wherein said mammal is a human.

13. The method of claim 11, wherein said composition is administered orally to said mammal.

14. The method of claim 11, wherein a unit dosage form of said composition containing from 1 to 500 mg per day per patient.

* * * * *